US00PP21808P2

(12) United States Plant Patent
Koppe

(10) Patent No.: US PP21,808 P2
(45) Date of Patent: Mar. 22, 2011

(54) *BEGONIA* PLANT NAMED 'ROXANNE'

(50) Latin Name: *Begonia×hiemalis*
Varietal Denomination: Roxanne

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 12/590,025

(22) Filed: Oct. 30, 2009

(51) Int. Cl.
*A01H 5/00* (2006.01)

(52) U.S. Cl. ..... Plt./346

(58) Field of Classification Search ..... Plt./346
See application file for complete search history.

(56) References Cited

PUBLICATIONS

UPOV-ROM GTITM, Plant Variety Database, 2010/05, GTI Jouve Retrieval Software, Citation for *begonia* plant 'Roxanne'.*

* cited by examiner

*Primary Examiner*—Susan B McCormick Ewoldt
(74) *Attorney, Agent, or Firm*—C. A. Whealy

(57) ABSTRACT

A new and distinct cultivar of *Begonia* plant named 'Roxanne', characterized by its upright, outwardly spreading and mounded plant habit; freely branching habit; dark green-colored leaves; double flowers with numerous tepals that are golden yellow in color and held above and beyond the foliage; and excellent postproduction longevity.

2 Drawing Sheets

Botanical designation: *Begonia×hiemalis.*
Cultivar denomination: 'ROXANNE'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'Roxanne'.

The new *Begonia* plant is a naturally-occurring whole plant mutation of *Begonia×hiemalis* 'Rachel', not patented. The new *Begonia* plant was discovered and selected by the Inventor as a single flowering plant from within a population of plants of 'Rachel' in a controlled greenhouse environment in Ermelo, The Netherlands in April, 2005.

Asexual reproduction of the new *Begonia* plant by vegetative cuttings taken in a controlled greenhouse environment in Ermelo, The Netherlands since June, 2005, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Roxanne'. These characteristics in combination distinguish 'Roxanne' as a new and distinct *Begonia:*

1. Upright, outwardly spreading and mounded plant habit.
2. Freely branching habit.
3. Dark green-colored leaves.
4. Double flowers with numerous tepals that are golden yellow in color and held above and beyond the foliage.
5. Excellent postproduction longevity.

Plants of the new *Begonia* differ primarily from plants of the parent, 'Rachel', in flower form as plants of 'Rachel' have semi-double flowers. In addition, leaves of plants of the new *Begonia* have double-serrate margins whereas leaves of plants of 'Rachel' have crenate margins.

Plants of the new *Begonia* can be compared to plants of *Begonia×hiemalis* 'Bbmil', disclosed in U.S. Plant Pat. No. 19,910. In side-by-side comparisons conducted in Ermelo, The Netherlands, plants of the new *Begonia* differed primarily from plants of 'Bbmil' in flower color as plants of 'Bbmil' had darker yellow-colored flowers. In addition, leaves of plants of the new *Begonia* had double-serrate margins whereas leaves of plants of 'Bbmil' had crenate margins.

Plants of the new *Begonia* can also be compared to plants of *Begonia×hiemalis* 'Blitz', not patented. In side-by-side comparisons conducted in Ermelo, The Netherlands, plants of the new *Begonia* differed primarily from plants of 'Blitz' in flower color and form as plants of 'Blitz' had deeper yellow-colored semi-double flowers. In addition, leaves of plants of the new *Begonia* had double-serrate margins whereas leaves of plants of 'Blitz' had crenate margins.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Roxanne' grown in a container.

The photograph on the second sheet is a close up view of the upper, side and lower surfaces of typical flowers of 'Roxanne' (left) and the upper and lower surfaces of typical leaves of 'Roxanne' (right).

DETAILED BOTANICAL DESCRIPTION

The aforementioned photographs and following observations and measurements describe plants grown during the late summer and early autumn in Ermelo, The Netherlands, under commercial practice in 13-cm containers in a glass-covered greenhouse. During the production of the plants, the average day temperature was 20° C. and the average night temperature was 18° C. Plants were eight weeks old when the photographs and description were taken. In the following description, color references are made to The Royal Horticultural Society Colour Chart, 2001 Edition, except where general terms of ordinary dictionary significance are used.

Botanical classification: *Begonia×hiemalis* 'Roxanne'.

Commercial classification: Elatior *Begonia.*

Parentage: Naturally-occurring whole plant mutation of *Begonia×hiemalis* 'Rachel', not patented.

Propagation:

*Type.*—By terminal vegetative cuttings.

*Time to develop roots.*—About 20 days at temperatures of 20° C.

*Time to produce a rooted young plant.*—About five weeks at temperatures of 20° C.

*Root description.*—Fine, fibrous; white to orange brown in color.

*Rooting habit.*—Freely branching; moderately dense; plants of the new *Begonia* have not been observed to form tubers.

Plant description:

*Plant form.*—Upright, outwardly spreading and mounded plant habit, inverted triangle; freely branching with good stem and stem base strength; flowers are double and positioned above the foliage.

*Growth habit.*—Vigorous growth habit; suitable for 11 to 14-cm containers; under optimal environmental and cultural conditions, usually about eight weeks are required to produce proportional 13-cm potted plants from cuttings; vegetative shoots are formed at basal nodes and flowering shoots are formed at upper nodes.

*Plant height.*—About 25 cm.

*Plant width.*—About 35 cm to 40 cm.

*Leaves.*—Arrangement: Alternate; simple. Developing leaves, length: About 4 cm. Developing leaves, width: About 7 cm. Fully expanded leaves, length: About 12 cm. Fully expanded leaves, width: About 18 cm. Shape: Roughly reniform, asymmetrical. Apex: Acute. Base: Cordate; asymmetric. Margin: Double-serrate. Texture, upper surface: Smooth, glabrous. Texture, lower surface: Pubescent. Venation pattern: Palmate. Color: Developing leaves, upper surface: Close to N137D. Developing leaves, lower surface: Close to 147B. Fully expanded leaves, upper surface: Darker than 147A; venation, close to 146B. Fully expanded leaves, lower surface: Close to 194A; venation, close to 146C. Petioles: Length: About 1.5 cm to 10 cm. Texture, upper and lower surfaces: Pubescent. Color, upper and lower surfaces: Close to N144A; with development, color becoming more green than 152D.

Flower description:

*Flowering habit.*—Double flowers with tepals arranged in axillary cymes; usually five to seven flowers per cyme; numerous cymes in flower simultaneously; flowers positioned above and beyond the foliage; flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 6 cm to 7 cm. Depth (height): About 3 cm to 3.5 cm.

*Flower buds.*—Length: About 1.2 cm to 2 cm. Diameter: About 3 mm to 4 mm. Color: Close to 150D.

*Tepals.*—Arrangement: Rosette. Quantity per flower: Numerous, typically about 100 per flower. Size: Outer tepals, length: About 3 cm. Outer tepals, width: About 3.5 cm. Inner tepals, length: About 2 cm. Inner tepals, width: About 2 cm. Shape: Rounded flabellate. Apex: Rounded. Margin: Mostly entire. Texture, upper and lower surfaces: Smooth, glabrous; satiny. Color: When opening, upper surface: Close to 7D. When opening, lower surface: Close to 8D. Fully opened, outer petals, upper surface: Close to 11A. Fully opened, outer petals, lower surface: Close to 10D. Fully opened, inner petals, upper surface: Close to 15D. Fully opened, inner petals, lower surface: Close to 16D.

*Flower bracts.*—Quantity/arrangement: Two, opposite. Shape: Ovate. Apex: Acute. Margin: Slightly senate to almost entire. Texture, upper and lower surfaces: Glabrous, smooth. Color, upper and lower surfaces: Close to 144B.

*Peduncles.*—Angle: Erect. Length: About 5 cm. Texture: Smooth, glabrous. Color: Close to 144C.

*Pedicels.*—Angle: Erect. Length: About 1.5 cm to 3 cm. Texture: Smooth, glabrous. Color: Close to 154D.

*Reproductive organs.*—Stamens: None observed. Pistils: None observed.

*Seed/fruit.*—Seed and fruit production have not been observed as reproductive organs are not formed.

Postproduction longevity: Plants last about six weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Roxanne' as illustrated and described.

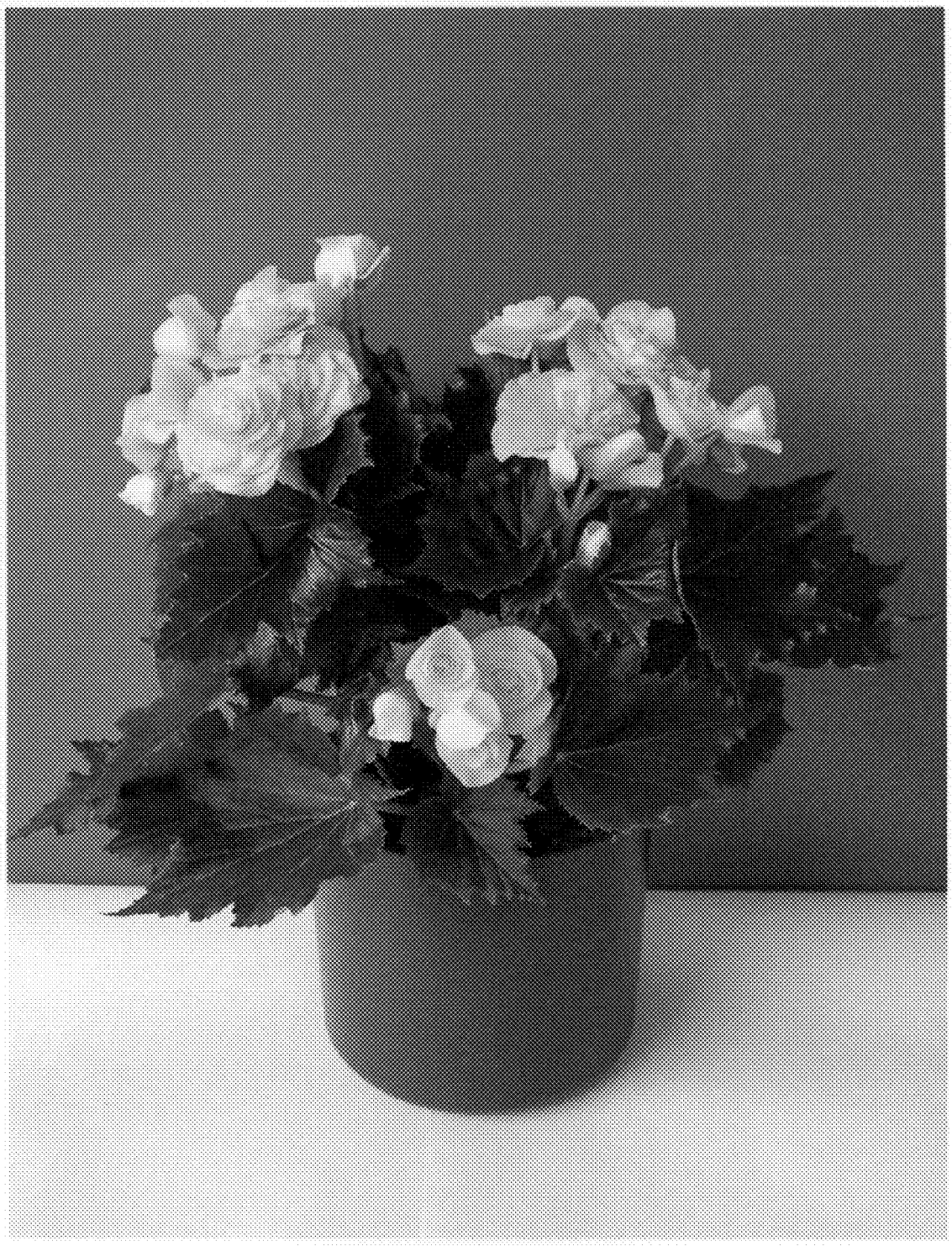

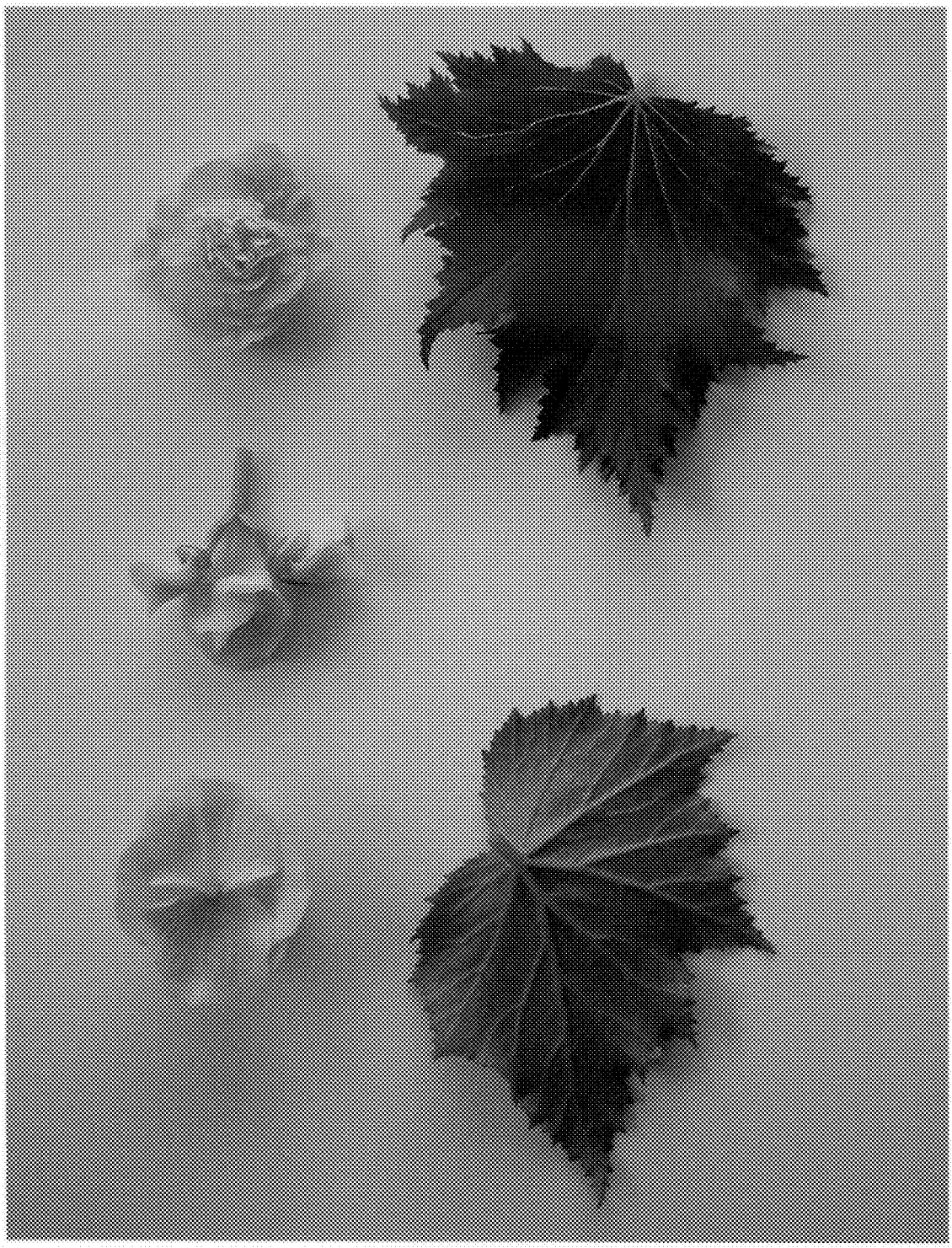

* * * * *